United States Patent [19]

Mertens

[11] Patent Number: 5,021,220
[45] Date of Patent: Jun. 4, 1991

[54] KIT FOR PREPARING RADIODIAGNOSTIC EXAMINATION COMPOSITIONS

[75] Inventor: John Mertens, Brussels, Belgium
[73] Assignee: Mallinckrodt, Inc., St. Louis, Mo.
[21] Appl. No.: 569,058
[22] Filed: Aug. 17, 1990

Related U.S. Application Data

[60] Division of Ser. No. 417,057, Oct. 4, 1989, abandoned, which is a continuation of Ser. No. 735,037, May 17, 1985, Pat. No. 4,942,231.

[30] Foreign Application Priority Data

May 24, 1984 [BE] Belgium ............................. 8491739
Jul. 5, 1984 [NL] Netherlands ...................... 8402138

[51] Int. Cl.⁵ ...................... A61K 49/02; B65D 69/00
[52] U.S. Cl. .................................. 424/1.1; 206/569
[58] Field of Search ............... 424/1.1 APS; 206/569

[56] References Cited

U.S. PATENT DOCUMENTS 4,031,198  6/1977  Jackson et al. ..................... 424/1.1
4,032,625  6/1977  Subramanian et al. .............. 424/1.1
4,942,231  7/1990  Mertens .......................... 424/1.1 X Primary Examiner—John S. Maples
Attorney, Agent, or Firm—Rothwell, Figg, Ernst & Kurz

[57] ABSTRACT

The invention relates to a method of preparing a chlorinated, brominated, radiobrominated, iodinated and/or radio-iodinated aromatic or heteroaromatic compound, in which the (hetero)aromatic nucleus optionally comprises one or more additional substituents, by reacting the corresponding halogenated or diazonium-substituted compound in the presence of a water-soluble acid and of copper ions as a catalyst with a likewise water-soluble chloride, bromide radiobromide, iodide or radio-iodide, in which the reaction is carried out in the presence of one or more reduction agents, which are stable in acid medium, in a quantity exceeding the quantity of catalyst. The invention also relates to a composition suitable for diagnostic examination and to a kit for the preparation thereof. The invention further relates to a method and an equipment for the preparation of said composition.

6 Claims, 1 Drawing Sheet

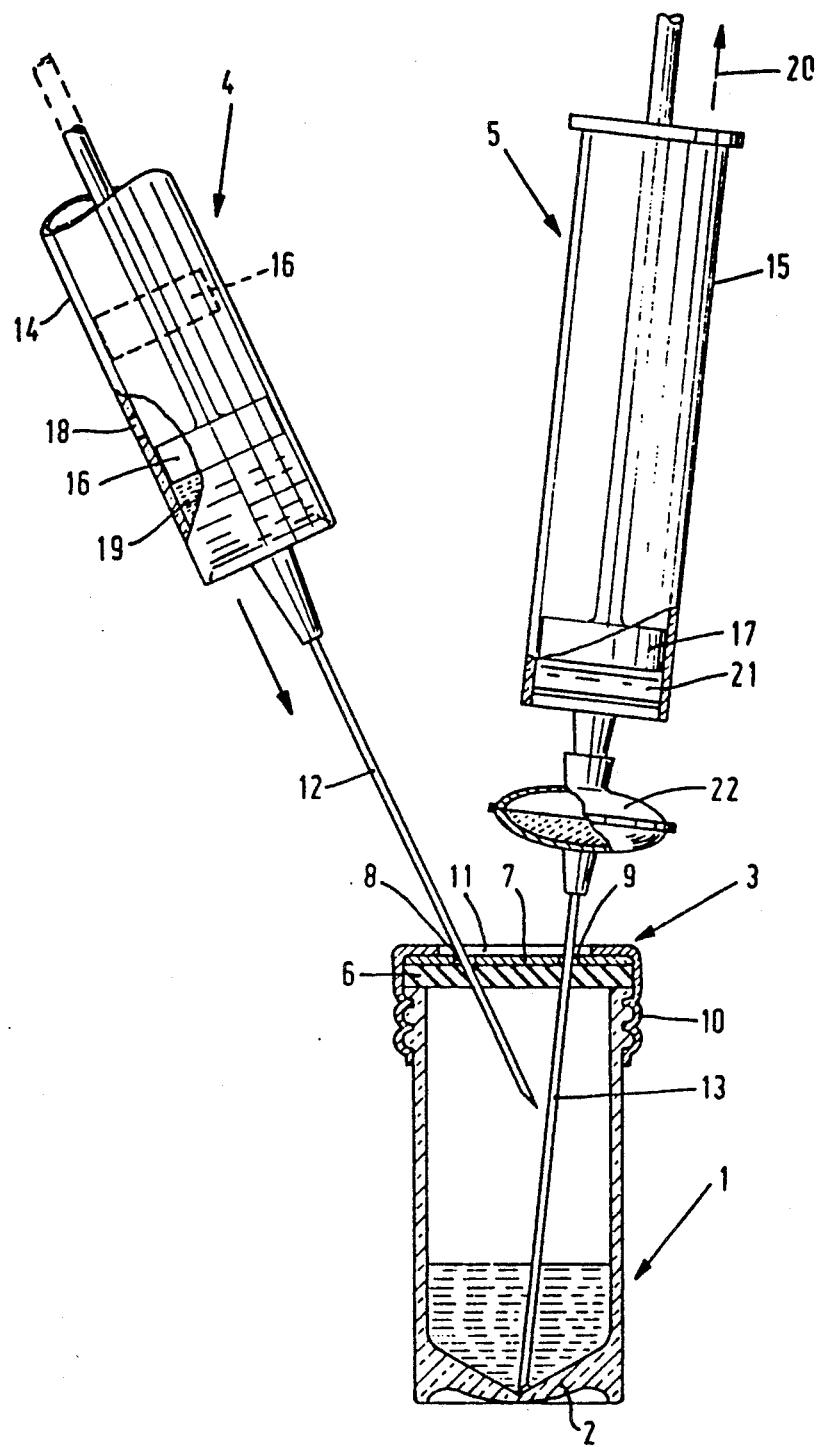

KIT FOR PREPARING RADIODIAGNOSTIC EXAMINATION COMPOSITIONS

This is a division of application Ser. No. 417,057, filed Oct. 4, 1989 now abandoned, which is a continuation of application Ser. No. 735,037 filed May 17, 1985 now U.S. Pat. No. 4,942,231.

Method of preparing a chlorinated, brominated, radiobrominated, iodinated and/or radioiodinated aromatic or heteroaromatic compound, and kit therefor.

The invention relates to a method of preparing a chlorinated, brominated, radiobrominated, iodinated and/or radioiodinated aromatic or heteroaromatic compound, in which the (hetero)aromatic nucleus optionally comprises one or more additional substituents, by reacting the corresponding halogenated or diazonium-substituted compound in the presence of a water-soluble acid and copper ions as a catalyst with a likewise water-soluble chloride, bromide, radiobromide, iodide or radioiodide.

Such aromatic substitution reactions in which, for example, a diazonium group is substituted by a halogen atom (Sandmeyer reaction) or a halogen atom is replaced by a different or a radiolabelled halogen atom, are frequently described in literature. However, in these reactions undesired by-products are often formed which lead to a contaminated final product. The reaction also often runs off incompletely, as a result of which the final product still contains undesired starting material.

This is a serious disadvantage, in particular for the preparation of substances having a pharmaceutical or diagnostic application for which a high degree of purity is required. An often elaborate purification process then is necessary to reach a purity which is acceptable for pharmaceutical application. This is the more important in preparing compounds for radiodiagnostic examination, because for these compounds a purification afterwards may give rise to a considerable reduction of radioactivity due to natural decay of the radioisotope.

Compounds for radiodiagnostic examination, i.e. radiolabelled compounds, may be used, for example, for the examination into deviations in shape and function of internal organs and into the presence and location of pathological processes in the body. For this purpose, a composition in which the radiolabelled compound is present can be administered to the patient, for example, in the form of an injectable liquid. By means of suitable detection device, for example, a gamma camera, images can be obtained by observing or recording the emitted radiation, of, for example, the organ, the body fluid or the pathological process in which the radiolabelled compound is incorporated.

A radiolabelled compound suitable for this purpose is radioiodinated o-iodohippuric acid or a salt thereof. This radiolabelled compound has been found to be particularly suitable for examining the renal function. The readily available sodium salt of o-iodohippuric acid, labelled with iodine-131, is often used for this purpose. Because the radiation characteristics of iodine-131 are less favourable and the half-life of said radioisotope is comparatively long for use in radiodiagnostics for examining the renal function, it has more recently been suggested to use iodine-123 labelled o-iodohippuric acid or a salt thereof. Iodine-123 has a comparatively short half-life, namely approximately 13 hours, as a result of which compounds of this radioisotope are on the one hand very suitable, for example, for examining the renal function but on the other hand may present logistic problems after the iostope has been produced in a cyclotron. Hawkins et al. described in Eur. J. Nucl. Med. 1982, 7, pp. 58–61 a fast method of preparing iodine-123-o-iodohippuric acid. In view of the above-mentioned logistic problems of iodine-123 labelled compounds, the said authors have suggested a kit preparation method in which the user himself, i.e. the clinic or the clinical laboratory, can prepare the radiolabelled compound by using a so-called kit. This kit comprises all the constituents which are necessary for the preparation, and usually instructions for use. A kit described by Hawkins et al. comprises the following constituents: acetate buffer, o-iodohippuric acid in 50% ethanol, an aqueous solution of copper sulphate and an aqueous solution of iodine-123 labelled sodium iodide. The combined ingredients were heated in an autoclave for 15 minutes at 121° C., producing the desired iodine-123-o-iodohippuric acid in a yield of 94%; 5% free iodine-123 was still present. The same result could be obtained by using a kit in a freeze-dried form in which a phosphate buffer was preferred to an acetate buffer.

The disadvantage of the above-described method is the still incomplete conversion to the desired radiolabelled compound. When used as a radiodiagnostic, the remaining free iodine-123 does not take part in the intended examination, but goes entirely to the thyroid gland which is thus burdened unnecessarily.

It has also been found that the use of an oxidant, for example manganic oxide, potassium permanganate or potassium iodate, instead of copper ions, does not result in a complete conversion. Upon radioiodinating rose bengal with iodine-131 in the presence of an oxidant, as described in U.S. Pat. No. 4,298,591, a conversion higher than approximately 90% could not be achieved.

Apparently, the preparation of radioiodinated amphetamine and derivatives thereof also presents great problems, as appears from European Patent No. 11858. After a technically unattractive preparation method in ethanol as a solvent in a closed tube at 121° C., the resulting product must be subjected to several purification steps.

Mills has described in Int. J. Appl. Rad. Isot., Vol. 33, 1982, pp. 467–468, the radioiodination of diatrizoic acid by reacting iodine-123 labelled sodiumiodide with diatrizoic acid in the presence of copper sulphate at a pH between 3 and 4. As will appear from the Examples, under the reaction conditions described by Mills, viz. heating for 15 minutes at 125° C., the desired radiolabelled product could be obtained in an average yield of only 82%. So also in this case the conversion is rather incomplete and the reaction temperature required, viz. 125° C., is unfavourable for kit purposes (see further).

It is the object of the present invention to provide a method for the preparation described in the opening paragraph which does not present the above-mentioned disadvantages and in which the desired product is produced in a high yield without interfering starting materials or by-products being present.

According to the invention this object can be achieved by performing the substitution reaction mentioned in the opening paragraph in the presence of one or more reduction agents, which are stable in acid medium, in a quantity exceeding the quantity of the catalyst used. It has been found surprisingly that as a result of this the yield of the product formed in the substitution reaction can be considerably increased, even up to approximately 100% in the preparation of e.g. radioiodinated o-iodohippuric acid, amphetamine derivatives, iodinated thyrosine, diatrizoic acid, iodinated benzylguanidine, and iodinated benzylpropanediamine derivatives.

The invention relates more in particular to the preparation of a brominated, radiobrominated, iodinated or radioiodinated aromatic or heteroaromatic compound, in which the (hetero)aromatic nucleus is a benzene nucleus, a naphthalene nucleus, a pyridine nucleus, a pyrimidine nucleus, a quinoline nucleus or an indole nucleus which comprises one or more additional substituents. Although the invention is particularly suitable for the preparation of radiolabelled compounds from the corresponding non-labelled compounds, the invention is by no means restricted thereto. (Hetero)aromatic compounds substituted with chlorine or non-labelled bromine or iodine can also be prepared from the corresponding halogen compounds or diazonium compounds by using the method according to the invention. Suitable non-radiolabelled iodine compounds which can be prepared by using the method according to the invention are iodine-containing contrast media, for example iophendylate and other ones on the basis of 2-, 2,4- or 2,4,6-substituted 1,3,5-triiodobenzene, for example, acetrizoic acid, adipiodone, amidotrizoic acid or diatrizoic acid, bunamiodyl, phenobutiodil, iobenzamic acid, iocarmic acid, iocetamic acid, iodamide, iodoxamic acid, ioglycamic acid, iopanoic acid, iopodic acid, iothalamic acid, ioxithalamic acid, metrizamide, metrizoic acid, tyropanic acid, and salts of the above-mentioned acids. Other suitable, non-radiolabelled compounds which can be prepared according to the invention from the corresponding halogen compounds of diazonium compounds are starting substances for radioiodinated diagnostics, for example, o-iodohippuric acid or salts thereof, iodoamphetamine or derivatives thereof, iodo-ω-phenyl fatty acids or salts thereof and rose bengal.

As stated hereinbefore, the invention is excellently suitable for the preparation of radiolabelled bromine or radiolabelled iodine compounds by reacting the corresponding non-radiolabelled bromine or iodine compounds in acid medium in the presence of a reduction agent with a water-soluble radiolabelled bromide or iodide. As a water-soluble bromide or iodide is preferably chosen an alkali metal bromide or iodide, for example, a sodium bromide or iodide or a potassium bromide or iodide. Radioisotopes suitable for this purpose are bromine-77, iodine-123, iodine-125 and iodine-131; as described hereinbefore, the best suitable of these iodine isotopes for use in radio-diagnostic compounds is iodine-123. Therefore, a iodine-123 labelled sodium iodide solution or potassium iodide-solution is preferably chosen for the substitution reaction. Various radioiodinated important diagnostics can simply and in a high yield be prepared in this manner, for example, radioiodinated o-hippuric acid and salts thereof, labelled iodoamphetamine and derivatives thereof, labelled iodo-ω-phenyl fatty acids and salts thereof, labelled iodinated thyrosines, such as labelled mono-, di-, tri- and tetraiodothyrosine, labelled 1,3,5-triiodobenzene derivatives, such as labelled diatrizoic acid and salts thereof, labelled halogenated benzylguanidine, such as m-iodobenzylguanidine, and labelled N,N,N'-trimethyl-N'-(2-hydroxy-3-methyl-5-iodobenzyl)-1,3-propanediamine. Labelled iodoamphetamine derivatives important for diagnostic purposes are labelled N-lower alkyl-substituted iodoamphetamines, for example, N-isopropyl-iodoamphetamine. Other interesting halogen-containing compounds which may be radioiodinated according to the invention are: rose bengal, N-iodoquinolyn-N,N'-dimethylpropanediamine, p-iodosulphonamide, N-iodophenylsulphonyl-N'-ethylurea, glibenclamed, 3-iodo-4-aminophenylethylamine, N,N-dimethyliodobenzylamine, substituted or non-substituted iodopyridines or iodopyridine-oxides, mono- and triiodobenzoic acid, N-[3-acetyl-4-(3-isopropylamino-2-hydroxy)propoxyphenyl]-iodobenzamide, iodinated indocyanine green, iodinated hydroxybenzylpindolol, iodinated thiouracil, iodinated estradiol, halogenated phenothiazines, halogenated benzodiazepines, halogenated metyrapone, halogenated butyrophenone derivatives, halogenated dibenzazepines, halogenated thyroid gland hormones as mentioned before, iodoantipyrine, and iodine-containing contrast media, for example iophendylate and other ones on the basis of 2-, 2,4-, and 2,4,6-substituted 1,3,5-triiodobenzene.

Reduction agents which are very suitable for use in the method according to the invention are Sn(II) salts. In addition to Sn(II) salts are preferably used one or more antioxidants, for example, metallic tin, ascorbic acid, citric acid, a monosaccharide or gentisic acid. Of these antioxidants ascorbic acid has been found to be particularly suitable for use together with a Sn(II) salt; when ascorbic acid is used, this acid may in addition have the function of water-soluble acid.

In addition to Sn(II) salts, other reduction agents stable in acid medium may successfully be used, for example, ascorbic acid, isoascorbic acid, citric acid, a monosaccharide, or a sulphite. The use of ascorbic acid as a reduction agent is to be preferred due to its extremely favourable influence on the desired substitution reaction, the ready availability and the suitability to use it in pharmaceutical compositions; moreover, ascorbic acid may serve as the water-soluble acid required for the reaction.

For example, radioiodinated o-iodo-hippuric acid or salts thereof, iodoamphetamine or derivatives thereof, iodo-phenyl fatty acids or salts thereof, iodobenzylguanidine, iodobenzylpropanediamine derivatives, and iodothyrosines can be prepared substantially quantitatively by reacting the corresponding non-radioactive bromine- or iodine-substituted compounds in the presence of a water-soluble acid and of copper ions as a catalyst with likewise water-soluble radioactive iodide, provided the reaction is carried out in the presence of ascorbic acid as a reduction agent.

Indeed, it has been found that in the preparation of radioiodinated o-iodohippuric acid or salts thereof, the catalyst may even be absent to still get a substantially quantititative result of the desired reaction. It is therefore to be considered a particular aspect of the invention that radioiodinated o-iodohuppuric acid or salts thereof can successfully be prepared by a simple reaction of the corresponding compound substituted with non-radioactive bromine or iodine with a water-soluble radioactive iodide in the presence of ascorbic acid as a reduction agent.

The reaction according to the invention can be readily carried out in an aqueous solution which comprises, if so desired, salts and one or more water-miscible organic solvents, for example, ethanol, methanol or acetone. Organic solvents as well as other auxiliary substances to improve the solubility have the disadvantage, however, of being potentially toxic. It is of great advantage that the reaction mixture can be directly introduced as a pharmaceutical composition in the blood stream of the living being without any further purification - for example, distilling-off organic solvent. In the reaction described by Hawkins et al in Eur. J. Nucl. Med. 1982, 7, 58-61 and in European patent 11858 a considerable quantity of ethanol is used, as a result of which the resulting reaction mixture is less suitable to be used as such as a radiodiagnostic. A particular advantage of the reaction according to the invention is that it gives a substantially quantitative result in a solution which is entirely free or substantially entirely free from organic solvent. The resulting reaction mixture can therefore be used directly for pharmaceutical applications by administering it, for example, intravenously or subcutaneously to a living being. The reaction is therefore preferably carried out in a sterile solution having a pH suitable for physiological application.

It is an extra aspect of the invention that the reaction can be carried out at a temperature which is suitable for use in a clinic or a clinical laboratory. This is important in particular for the preparation of compounds labelled with radioactive bromine or iodine. These compounds, having a comparatively short life in connection with natural decay of the radioisotope used, can then be prepared in situ by the user and be used immediately thereafter. It has been found that the desired substitution reaction proceeds excellently at a temperature of approximately 121° C., a temperature at which compositions for intravenous or subcutaneous administration have to be sterilized. Although some clinics or clinical laboratories have the disposal of an autoclave with which sterilizations at 121° C. can be carried out, this is not the general rule. A preparation on or in a water bath, however, can simply be realized in any clinic and any clinical laboratory. It is therefore of particular importance that the reaction according to the invention has been found to result in the desired product quanititatively already at approximately 100° C. This is another great advantage as compared with the methods described by Hawkins et al. and by Mills, in which temperatures of 121° C. and 125° C. respectively were necessary for conversions to only 94% and 82% respectively.

The invention also relates to a composition suitable for diagnostic examination which comprises, in addition to a pharmaceutically acceptable formulation liquid and/or one or more auxiliary substances, a iodine-containing contrast medium which has been prepared by using the method according to the invention, and to a composition which is suitable for diagnostic examination, which comprises a radioiodinated diagnostic, and which has also been prepared by using the method according to the invention.

The invention further relates to a method of preparing the above injectable composition. This method is carried out in that a pharmaceutically acceptable formulation liquid, which may comprise one or more auxiliary substances and is accomodated in at least one supply syringe, is added to the radioiodinated diagnostic, which radiodiagnostic containing substance is accomodated in a vial, sealingly closed with a pierceable stopper, said addition being carried out by piercing the stopper of said vial with the needle or needles of said supply syringe or syringes, and by then allowing the formulation liquid in said supply syringe or syringes to communicate with the atmospheric pressure to enable said liquid to reach the substance in the vial through the needle or needles, and that the composition in the vial thus obtained is then transferred to an injection syringe by piercing the stopper of said vial with the needle of said injection syringe and by then sucking the composition into the injection syringe, during which addition and/or transfer said formulation liquid and/or injectable composition preferably flow(s) through at least one sterilizing filter.

If said addition and transfer are carried out in a sterile atmosphere, e.g. under laminar flow conditions, sterilizing filters may be omitted.

BRIEF DESCRIPTION OF THE FIGURE

The sole FIGURE is a new elevational view partially schematic with portions broken away and in partial cross-section, of equipment forming a kit in accordance with the present invention.

The invention also relates to an equipment for carrying out the above method, which equipment comprises (a) at least one supply syringe, provided with a cylindrical barrel for accomodating a formulation liquid, to which barrel a hollow needle is sealingly connected and in which barrel a plunger is movably positioned, the cylindrical side-wall of said barrel being provided with at least one aperture in such distance from the attached needle, that the formulation liquid to be accomodated in the barrel can be separated from the aperture in the barrel wall by means of the plunger, but that by withdrawing the plunger said aperture can allow said formulation liquid to communicate with the atmospheric pressure outside the syringe, (b) a vial for accomodating a radiodiagnostic containing substance, which vial is sealingly closed with a pierceable stopper, and (c) an injection syringe, provided with a cylindrical barrel for accomodating an injectable composition, to which barrel a hollow needle is sealingly connected, if desired, through an intermediately positioned sterilizing filter means, the needle having a length sufficient for reaching the bottom of the vial after having pierced the stopper of said vial, and in which barrel a plunger is movably positioned.

Moreover the invention relates to the above-defined syringe for said equipment, provided with a cylindrical barrel for accomodating a formulation liquid.

The invention further relates to a method of radioassaying a warmblooded living being, in particular a human being, by administering the above radiodiagnostic composition to the being, in which the quantity of radioactivity administered should be sufficient for detection by external imaging. The being is then subjected to external imagining, for example with a gamma camera, to detect the accumulated radioactivity and thus to determine the location thereof in the body, or to establish the function of an organ. A quantity of radioactive material to be administered which is sufficient for detection by external imaging is approximately 0.1 to approximately 10 millicurie per 70 kg of bodyweight; the radioactive material is preferably administered in a quantity of 0.1 to 7 millicurie per 70 kg of body weight.

As described hereinbefore, the reaction according to the invention for the preparation of radioactive compounds is excellently suitable for a kit preparation. This means that a so-called "cold" kit in which all the ingredients for the preparation reaction are present with the exception of the radioactive iodide or bromide, is placed available to the user. The radioactive material is placed to the user's disposal separately. The user himself can now perform the reaction according to the invention by taking the kit destined for preparing the radiolabelled compound which he desires and mixing the ingredients thereof with the radiolabelled iodide or bromide, by heating the resulting mixture for a short period of time, for example at 100° C., a composition suitable for diagnostic examination is obtained. If desired, a formulation liquid may be added to the mixture prior to or after heating. The ingredients are preferably present in the kit in a freeze-dried form; this is in favour of the stability.

It will be obvious from the above that the invention relates also and in particular to a kit for preparing a composition suitable for radiodiagnostic examination. In addition to the bromine-substituted or iodine-substituted aromatic or heteroaromatic compound in which the (hetero)-aromatic nucleus optionally comprises one or more additional substituents, to a water-soluble acid, a copper salt and, if desired, a pharmaceutically acceptable formulation liquid and/or auxiliary substances, the said kit comprises a reduction agent as described hereinbefore. The kit furthermore comprises instructions for use with a prescription for carrying out the method.

Finally, the invention also relates to a kit for preparing radioiodinated o-iodohippuric acid or a salt thereof, comprising the non-labelled compound, if desired a pharmaceutically acceptable formulation liquid and/or auxiliary substances, and ascorbic acid as a reduction agent. This kit also comprises instructions for use.

The invention will now be described in greater detail with reference to the ensuing specific examples.

EXAMPLE I 3.3 μmol Cu(II) (solution of 32.5 mg of $CuSO_4.5H_2O$ per 10 ml of water), 43 μmol of ascorbic acid, 0.3 μmol of N-isopropyl-para-iodoamphetamine.HCl, 30 μl of a iodine-123 labelled sodium iodide solution having a specific activity of 0.5 mCi/μl and 150 μl of water were heated, after mixing, in a closed vial at 100° C. for 30 minutes. The resulting labelling efficiency of the radiolabelled product was determined by radio-HPLC and was higher than 99%, while no radioactive by-products could be detected. Nor could non-labelled by-products be detected by means of UV-spectroscopy.

The same results were obtained when in addition 0.4 μmol of Sn(II) were added.

EXAMPLE II

50 μl of $Cu(NO_3)_2$ in an acetic acid (96%) solution (1.3 mg/ml), 1 mg of $SnCl_2.2H_2O$ and 1 mg of N-isopropyl-para-iodoamphetamine.HCl were mixed in a closed reaction vial. A chip of metallic tin and 20 μl of iodine-123 containing sodium iodide solution (specific activity 0.5 mCi/μl) were then added. The vial was then heated to 170° C. for 30 minutes. The resulting labelling efficiency, determined by radio-HPLC, was higher than 99%. The reaction product thus obtained was then brought at pH 10 to 11 with a 1 molar NaOH solution and chromatographed over a micro column with Prep.-Bondapack C18 (55–105μ; reg. trademark) packing. The column was then rinsed with 10 ml of $H_2O$ and the N-isopropyl-p-I-amphetamine was eluted quantitatively with 2-3 ml of acidified ethanol.

When instead of iodine-123 sodium iodide a bromine-77 containing sodium bromide solution was used, the radiobromine-labelled amphetamine derivative could be prepared under substantially the same conditions.

Iodine-123 labelled N-isopropyl-para-iodoamphetamine could also be obtained by starting from N-isopropyl-para-bromoaphetamine, by reacting it with iodine-123 labelled sodium iodide.

EXAMPLE III 0.2 mg of ortho-iodohippuric acid, 2 mg ascorbic acid, 1-3 μmol $CuSO_4$, 0.5 ml $H_2O$ and radioactive iodide (50 μl of a sodium iodide solution labelled with iodine-123; activity 25 mCi) were mixed in a closed vial and heated at substantially 100° C. for 5 minutes.

By means of radio-HPLC it was demonstrated that the labelling efficiency was substantially 100%, while no radioactive or non-labelled by-products could be detected (UV).

The reaction has been carried out with the same result using a iodine-131 labelled sodium iodide solution.

EXAMPLE IV 1 mg of p-bromophenylhexadecane carboxylic acid, 0.3 ml $MeOH/H_2O$ (90/10), 2 μmol $CuSO_4$, 4 mg of ascorbic acid and 50 μl of a iodine-123 labelled sodium iodide solution (activity 25 mCi) were heated at 150° C. in a closed reaction vessel for 1 hour.

The desired iodine-123 labelled product was obtained in a labelling efficiency of more than 90%, while substantially no by-products were formed.

EXAMPLE V 1 mg of p-iodophenylhexadecane carboxylic acid, 0.3 ml of $MeOH/H_2O$ (90/10), 2 μmol $CuSO_4$, 4 mg of ascorbic acid and 5 μl of a iodine-123 labelled sodium iodide solution (activity 2.5 mCi) were heated at 100° C. in a closed reaction vial for 30 minutes. The labelling efficiency was substantially 100%; this was determined by means of radio-HPLC.

EXAMPLE VI

Kit preparation for an injectable radioiodinated N-isopropyl-p-iodoamphetamine solution, as well as the use of said solution.

The following components were added together in the given sequence:
(1) 2 mg of N-isopropyl-p-iodoamphetamine.HCl (5.9 μ-mol),
(2) 10 mg of ascorbic acid
(3) 460 μl of water,
(4) 40 μl of $CuSO_4$ solution (5.2 μmol), and
(5) 10 μl of $SnSO_4$ solution (0.44 μmol).

After freeze-drying, the mixture was added under nitrogen to a sterile closed vial, after which 0.5 ml of sterile oxygen-free water and 10 μl iodine-123 labelled sodium iodide solution were successively added (5 mCi). The vial was heated at 100° C. for 30 minutes. In order to obtain an isotonic solution having a pH of approximately 6 suitable for injection, 1.5 ml of a sterile aqueous solution containing per millilitre 6 mg of NaCl. 3.3 mg of ascorbic acid and 2.42 mg of $Na_2CO_3.10H_2O$ were added to the resulting reaction mixture.

The labelling efficiency of the resulting composition was determined by means of radio-HPLC and was over 99%. Non-labelled by-products could not be detected (UV). When no sterile solutions were used, the composition was sterilized afterwards by filtration over a 0.22μ filter; the composition then did not differ from the above one.

The sterilized composition was administered intravenously to a patient in a quantity of 2.5 mCi. Excellent scintigraphic images of the brains were obtained by means of a gamma camera.

EXAMPLE VII

Preparation of radioiodinated o-iodohippuric acid and kit for a composition provided with the said radiodiagnostic.

1 ml of sterile oxygen-free water and 20 μl of a sterile iodine-123 labelled sodium iodide solution were added successively to 1 mg of o-iodohippuric acid sodium salt and 4 mg of ascorbic acid in a sterile closed vial under nitrogen (total activity 10 mCi). The vial was heated at 100° C. for 10 minutes. The labelling efficiency was determined by means of radio-HPLC and was approximately 100%. Labelled or non-radioactive by-products were not detected. In order to obtain an isotonic solution having a pH suitable for injection, 1 ml of a sterile aqueous solution was added comprising 4 mg of ascorbic acid, 14 mg of NaCl and 5 mg of $Na_2CO_3.10H_2O$.

When no sterile solutions were used, the resulting compositions was sterilized afterwards as described in Example VI.

When a iodine-131 labelled sodium iodide solution was used, the iodine-131 labelled o-iodohippuric acid was obtained with the same labelling efficiency.

EXAMPLE VIII

Kit preparation for an injectable radioiodinated N-isopropyl-p-iodoamphetamine (IAMP) solution, as well as the use of said solution.

The following components were added together in the given sequence:
(1) 2 mg of pure N-isopropyl-p-iodoamphetamine sulphate
(2) 10 mg of L-ascorbic acid
(3) 5 mg of gentisic acid
(4) 1 mg of $SnSO_4$
(5) 4.5 mg of sodium citrate.$2H_2O$
(6) 1.2 mg of $Na_2SO_4$
(7) 1000 μl of oxygen-free water
(8) 40 μl of $CuSO_4$ solution (32.5 mg $CuSO_4.5H_2O$/10 ml $H_2O$).

The mixture was added through a 0.22μ sterilizing filter to a sterile and apyrogen vial, then freeze-dried in a sterile nitrogen atmosphere and septum-closed under these conditions.

For clinical preparation 1 ml of sterile oxygen-free water and 5 μl of sterile iodine-123 labelled sodium iodide solution (2 mCi) or 1 ml of sterile iodine-123 labelled sodium iodide solution (containing the required activity) were added. The septum-closed vial was heated at 100° C. for 30 minutes.

The obtained solution was isotonic and of injectable pH. The labelling efficiency of the resulting composition, as determined by means of radio-HPLC, was over 99% (average of 20 experiments). Non-labelled by-products could not be detected (UV detection).

The composition was administered intravenously to a patient in a quantity of 2 to 4 mCi. Excellent scintigraphic images of the brains were obtained with both a planar (2 mCi) and SPECT (4 mCi) γ-camera.

The composition was found stable for at least 24 hours. Use of the $^{123}$-I-solution in amounts varying from 5 to 50 μl (5 to 25 mCi) yielded equal results.

EXAMPLE IX

Kit preparation for an injectable radioiodinated o-iodo-hippuric acid solution, as well as the use of said solution.

2 mg of pure o-iodo-hippuric acid
5 mg of gentisic acid
10 mg of L-ascorbic acid
1 mg of $SnSO_4$
1000 μl of oxygen-free water
1 μl of a $CuSO_4$ solution (300 μg $CuSO_4.5H_2O$/10 ml)

The above mixture was treated and freeze-dried as mentioned in Example VIII.

The clinical preparation was carried out in two steps:
(1) 1 ml of sterile oxygen-free water and 2.5 μl of sterile $^{123}$-I-solution (1 mCi) or 1 ml of a sterile $^{123}$-I-solution (containing the required activity) were added. The septum-closed vial was heated at 100° C. for 20 minutes.
(2) 1 ml of a sterile oxygen-free aqueous solution containing 12 mg of sodium citrate and 23 mg of $Na_2SO_4$/ml were added to the reaction mixture to obtain a sterile isotonic solution of injectable pH. A labelling of 99% has been obtained. HPLC control showed neither labelled nor unlabelled side products. The composition was stable for at least 24 hours.

The composition administrated was used with success for non invasive kidney studies (1 mCi intravenously injected).

Use of the $^{123}$-I-solution in amounts varying from 2.5 to 50 μl (1 to 20 mCi) yielded equal results.

EXAMPLE X

Kit preparation for an injectable radioiodinated m-iodobenzylguanidine (MIBG) solution as well as the use of said solution.

The following components were added together in the given sequence:
(1) 2 mg of pure m-iodobenzylguanidine sulphate
(2) 10 mg of L-ascorbic acid
(3) 5 mg of citric acid
(4) 0.5 mg of $SnSO_4$
(5) 500 μl of oxygen-free water
(6) 10 μl of $CuSO_4$ solution (32.5 mg $CuSO_4.5H_2O$/10 ml $H_2O$).

The above mixture was treated and freeze-dried as described in example VIII.

The clinical preparation was carried out in two steps:
1) 500 μl of sterile oxygen-free water and 10 μl of sterile $^{123}$-I-solution (4 mCi) or 1 ml of a sterile $^{123}$-I-solution (containing the required activity) were added. The septum-closed vial was heated at 100° C. for 20 minutes.
2) 1.5 ml of a sterile oxygen-free aqueous solution containing 5 mg of sodium citrate and 30 mg of $Na_2SO_4$/1.5 ml water were added to the reaction mixture to obtain a sterile isotonic solution of injectable pH. A labelling yield of >99% has been obtained. HPLC control did not show any labelled or unlabelled by-products. The composition was stable for at least 15 hours.

The composition administered intravenously (4 mCi per 70 kg body weight) was used with success for the γ-scintigraphic diagnosis of neuroblastoma and phenochromocytoma. Use of the $^{123}$-I-solution in amounts varying from 10 to 50 μl (4 to 20 mCi) yielded equal results.

The above-described labelling conditions and clinical preparation also yielded pure $^{131}$I-MIBG (>99% labelling yield) at a dose of 2 mCi $^{131}$I.

EXAMPLE XI

Kit preparation for an injectable radioiodinated p-iodophenyl-pentadecanoic acid (PIPPA) solution.

The following components were added together in a 3 ml vial in nitrogen atmosphere.

0.4 mg of p-iodophenylpentadecanoic acid
0.6 mg of SnSO$_4$
2.3 mg of L-ascorbic acid
50 μl of oxygen-free water
10 μl of CuSO$_4$ solution (32.5 mg CuSO$_4$.5H$_2$O/10 ml)
100 μl ethanol
5 μl iodine-123 labelled sodium iodide solution (2 mCi)

The septum-closed vial was heated at 100° C. during 30 minutes. A labelling yield of 98.5% was obtained. After cooling down the solution was made up with 1.8 ml of a 6% Human serum albumine solution and sterilised through a 0.22μ filter and recovered in a sterile and pyrogenfree vial filled with nitrogen gas.

Use of the $^{123}$-I-solution in amounts varying from 5 to 50 μl (2 to 25 mCi) yielded equal results.

EXAMPLE XII

Kit preparation for an injectable radioiodinated N,N,N'-trimethyl-N'-(2-hydroxy-3-methyl-5-iodobenzyl)-1,3-propanediamine (HIPDM) solution, as well as the use of said solution.

The following components were added together in the given sequence:
1) 2 mg of pure N,N,N'-trimethyl-N'-(2-hydroxy-3-methyl-5-iodobenzyl)-1,3-propanediamine
2) 10 mg of L-ascorbic acid
3) 5 mg of gentisic acid
4) 1 mg of SnSO$_4$
5) 4.5 mg of sodium citrate.2H$_2$O
6) 1.2 mg of sodium sulphate
7) 1000 μl of oxygen-free water
8) 40 μl of CuSO$_4$ solution (32.5 mg CuSO$_4$.5H$_2$O/10 ml H$_2$O The above mixture was added through a 0.22μ sterilizing filter to a sterile and pyrogenfree vial and was freeze-dried in a sterile nitrogen atmosphere and septum-closed under these conditions. For clinical preparation 1 ml of sterile oxygen-free water and 5 μl of sterile iodine 123-labelled sodium iodide solution (2 mCi) or 1 ml of sterile iodine-123 labelled sodium iodide solution (containing the required activity) were added. The septum-closed vial was heated at 100° C. for 30 minutes. The obtained solution is isotonic and of injectable pH. A labelling yield of 99% has been obtained. Neither labelled nor unlabelled side products have been observed.

The composition is administered intravenously to a patient (2 to 5 mCi amounts) for brainscintigraphy. Use of the $^{123}$-I-solution in amounts varying from 5 to 50 μl (2-25 mCi) yielded equal results.

EXAMPLE XIII

Radioiodination of mono-iodothyrosine

The following components were added together in the given sequence:
1) 0.3 mg of pure mono-iodothyrosine
2) 10 mg of L-ascorbic acid
3) 230 μl of oxygen-free water
4) 70 μl of CuSO$_4$ solution (32.5 mg CuSO$_4$.5H$_2$O/10 ml)
(5) radioiodide solution in amounts varying from 5 to 50 μl The above mixture was heated in a septum-closed vial during 2 minutes at 100° C. A labelling yield of more than 99% was obtained. After 10 minutes of heating no side-products could be observed.

EXAMPLE XIV

Radioiodination of di-iodothyrosine 0.3 mg of di-iodothyrosine was labelled under identical conditions as described for mono-iodothyrosine (example XIII). A labelling yield of at least 99% was obtained within 2 minutes.

EXAMPLE XV

Radiodination of diatrizoic acid.

The following compounds were added together in the given sequence:
1) 0.6 mg of pure diatrizoic acid
2) 0.6 mg of citric acid
3) 280 μl of oxygen-free water
4) 20 μl of CuSO$_4$ solution (32.5 mg CuSO$_4$.5H$_2$O/10 ml)
5) radioiodide solution in amounts varying from 5 to 50 μl.

The above mixture was heated at 100° C. in a septum-closed vial during 10–15 minutes. A labelling yield higher than 99% was obtained. No labelled or unlabelled side-products could be detected.

By comparison diatrizoic acid was radiolabelled according to the method described by Mills (Int. J. Appl. Rad. Isot., Vol 33, 1982, pp. 467–468). 0.16 mCi iodine-123 labelled sodiumiodide solution was added to 1 ml of a solution containing 2.5 mg diatrizoic acid and 0.25 mg CuSO$_4$.5H$_2$O per ml.

Prior to adding the radioiodide the pH of the solution was adjusted to 3.4 with 1N hydrochloric acid.

The mixture was heated for 15 minutes at 125° C. After cooling to room temperature 1.5 ml phosphate buffer (6.185 gram of dibasic sodiumphosphate per 100 ml water) was added to adjust the pH to 7.0.

The solution was stirred for two minutes and passed through a 0.22 micron filter.

The radiochemical purity was determined on HPLC using a Hewlett Packard RP8 10μ (dichrosorb) column and methanol/water/acetic acid 5/95/0.15 as the mobile phase.

In four similar experiments an average yield of only 82% I-123 diatrizoic acid was found.

EXAMPLE XVI

Presence of Sn (II) in the reaction mixture; influence of the presence of higher oxidation states than I$^-$ on the reaction rate.

In addition Sn (II) can also achieve the reduction of entities with a higher oxidation state than radioiodide, such as radioiodate, which can be present in amounts up to more than 2–3% in commercially available radioiodide solutions. It renders those species available as iodide for the nucleophilic exchange reaction, e.g. the exchange of iodine by radiolabelled iodine, thus allowing to obtain the high labelling yields mentioned in the Examples before.

To determine the influence of Sn (II) on the radioiodination when using $^{123}$-I-solutions of different qualities, the radioiodination was carried out as described in Examples VIII to XII with radioiodide solutions from various suppliers. It is well-known in the art, that the labelling yields of earlier described methods are influenced by the quality of the radioiodide solutions. It has now been found, however, that in the above experiments the labelling yields did not differ substantially.

EXAMPLE XVII

Equipment for preparing an injectable composition. The equipment is shown in the Figure, wherein with reference numeral 1 a vial is denoted with an internally conical bottom 2. The vial is sealingly closed with a stopper 3. Stopper 3 of vial 1 comprises a pierceable rubber disk 6, at the upper side covered by an aluminium sheet 7 wherein two apertures 8 and 9 are recessed. A screw cap 10 with a central aperture 11 keeps the rubber disk 6 and the aluminium sheet 7 tightly clamped on the upper edge of vial 1. The reaction mixture, e.g. the kit preparation together with the radioiodide solution, is accomodated in the vial and the reaction is carried out by heating the reaction mixture at the desired temperature, e.g. 100° C. After the reaction is complete, the vial comprises a solution of the product, e.g. the radioiodinated product, thus obtained. In the Figure the supply syringe is denoted with reference numeral 4, the injection syringe with 5. Both syringes are provided with hollow needles 12 and 13 respectively, which can be stuck through the apertures 8 and 9 in the aluminium sheet and through the rubber disk to allow communication of the interior of the syringes with that of the vial. The syringes further comprise cylindrical barrels 14 and 15 respectively, in which plungers, 16 and 17 respectively, are movably positioned. Supply syringe 4 is intended for accomodating a formulation liquid, e.g. an isotonic solution, and is provided with an aperture 18 in the side wall of its barrel 14. The aperture 18 has such a distance from the needle mount, i.e. the mounting means of the needle to the barrel, that in the original position the plunger 16 separates the aperture 18 from the room 19 wherein the formulation liquid is accomodated, whereas said room 19 can be allowed to communicate with the atmospheric pressure outside the syringe via the aperture by withdrawing plunger 16 up to above aperture 18. This latter position of the plunger 16 is denoted in the Figure in dotted lines. Injection syringe 5 can accomodate the injectable composition in room 21 and is provided with a sterilizing filter 22, e.g. of 0.22μ, detachably connected between injection needle 13 and the needle mount for mounting the needle to barrel 15.

When the equipment shown in the Figure is used to prepare an injectable composition, the stopper 3 of vial 1 is pierced (at 8) by needle 12 of supply syringe 4. In the vial a solution of the product to be formulated is accomodated. The supply syringe contains in room 19 a formulation liquid, e.g. an isotonic solution. The supply syringe is then positioned as shown in the Figure; the needle tip does not contact the solution in the vial. In the same way the needle 13 of injection syringe 15 is stuck through stopper 3 of vial 1 (at 9). The injection syringe is also positioned as shown in the Figure; the needle extends into the solution to the conical bottom of the vial so that the needle tip (nearly) contacts this bottom. Injection syringe 15 is empty.

Thereupon plunger 16 of syringe 4 is withdrawn up to above aperture 18 (dotted lines), resulting in a communication between the formulation liquid in this syringe with the atmospheric pressure. As a consequence of this the formulation liquid flows through the hollow needle 12 into the vial (see the arrow) and can easily be mixed with the contents of the vial by shaking this vial.

The injectable composition thus obtained is then transferred from the vial into the injection syringe 5 by withdrawing plunger 17 in the direction of arrow 20. To collect a sterile composition in room 21 of barrel 15 of this injection syringe, the composition reaches said room 21 via sterilizing filter 22.

In a different embodiment of the present invention aperture 18 of supply syringe 4 can be provided with a sterilizing filter. Then sterilizing filter 22 may be omitted. This embodiment is preferably used when the contents of vial 1 are already in a sterile condition.

Stabilizing filters may be omitted completely, when the equipment is installed in a sterile room, e.g. in a laminar flow unit.

I claim:

1. A kit for the preparation of a radiodiagnostic examination composition, comprising a bromine bromine-, or iodine-substituted aromatic or heteroaromatic starting compound, a water-soluble acid, a copper salt, a reducing agent stable in an acid medium, and instructions for preparing the composition by reacting the starting compound with a water-soluble chloride, bromide radiobromide, iodide or radioiodide in the water-soluble acid in the presence of (a) the copper salt as a catalyst and (b) the reducing agent in a quantity exceeding the quantity of the catalyst.

2. A kit according to claim 1 wherein the starting compound comprises a member of the group consisting of iodophendylate, a 2-, 2,4- or 2,4,6-substituted 1,3,5-triiodobenzene, o-iodohippuric acid or a pharmaceutically-acceptable salt thereof, iodoamphetamine or a pharmaceutically-acceptable derivative thereof, iodo-ω-phenyl fatty acid or a pharmaceutically-acceptable salt thereof, and rose bengal.

3. A kit according to claim 1 or 2 wherein the reducing agent is a member of the group consisting of a pharmaceutically-acceptable Sn(II) salt, ascorbic acid, isoascorbic acid, citric acid, a monosaccharide, gentisic acid and pharmaceutically-acceptable salts of said acids.

4. A kit according to claim 1 wherein the starting compound is o-iodohippuric acid or a pharmaceutically-acceptable salt thereof and the reducing agent is ascorbic acid.

5. A kit according to claim 1 wherein the instructions include the steps of
   (I) reacting the starting compound with a water-soluble iodide or radioiodide in said acid medium in the presence of (a) copper ions as a catalyst and (b) said reducing agent, which is stable in said acid medium, in a quantity exceeding the quantity of the catalyst;
   (II) placing the compound obtained in step (I) in a vial closed with a pierceable stopper;
   (III) adding a pharmaceutically-acceptable formulation liquid to the vial; and
   (IV) withdrawing the liquid from the vial through a sterilizing filter and into an injection syringe.

6. A kit according to claim 1, further comprising:

(a) a supply syringe comprising a barrel, a hollow needle connected to the barrel and a plunger disposed within the barrel, a side wall of the barrel comprising an aperture spaced a distance from the needle whereby formulation liquid within the barrel can be separated from the aperture by the plunger, but by withdrawing the plunger the formulation liquid can communicate through the aperture with an atmosphere outside the syringe;

(b) a vial, for accommodating a radiodiagnostic composition, comprising a pierceable stopper; and (c) an injection syringe.

* * * * *